US012765863B2

(12) United States Patent
Brattain et al.

(10) Patent No.: US 12,765,863 B2
(45) Date of Patent: Oct. 20, 2026

(54) SYSTEMS AND METHODS FOR PORTABLE ULTRASOUND GUIDED CANNULATION

(71) Applicants: Massachusetts Institute of Technology, Cambridge, MA (US); The General Hospital Corporation, Boston, MA (US)

(72) Inventors: Laura J. Brattain, Cambridge, MA (US); Anthony E. Samir, Cambridge, MA (US); Brian A. Telfer, Cambridge, MA (US); Nancy DeLosa, Cambridge, MA (US); Lars Gjesteby, Cambridge, MA (US); Theodore T. Pierce, Cambridge, MA (US); Matthew Johnson, Cambridge, MA (US); Westin Hill, Cambridge, MA (US); Andres Chamorro, Cambridge, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 18/976,529

(22) Filed: Dec. 11, 2024

(65) Prior Publication Data

US 2025/0268564 A1 Aug. 28, 2025

Related U.S. Application Data

(62) Division of application No. 16/995,637, filed on Aug. 17, 2020, now Pat. No. 12,193,872.

(Continued)

(51) Int. Cl.
*A61B 8/00* (2006.01)
*A61B 8/08* (2006.01)
(Continued)

(52) U.S. Cl.
CPC .............. *A61B 8/12* (2013.01); *A61B 8/0841* (2013.01); *A61B 8/0875* (2013.01);
(Continued)

(58) Field of Classification Search
None
See application file for complete search history.

(56) References Cited

U.S. PATENT DOCUMENTS 6,379,307 B1 4/2002 Filly
2002/0133079 A1 9/2002 Sandhu
(Continued)

FOREIGN PATENT DOCUMENTS

EP 2279695 A1 2/2011
EP 3260295 A1 12/2017
(Continued)

*Primary Examiner* — Amal Aly Farag
(74) *Attorney, Agent, or Firm* — Quarles & Brady, LLP

(57) ABSTRACT

Systems and methods are provided for semi-automated, portable, ultrasound guided cannulation. The systems and methods provide for image analysis to provide for segmentation of vessels of interest from image data. The image analysis provides for guidance for insertion of a cannulation system into a subject which may be accomplished by a non-expert based upon the guidance provided. The guidance may include an indicator or a mechanical guide to guide a user for inserting the vascular cannulation system into a subject to penetrate the vessel of interest.

19 Claims, 12 Drawing Sheets

Related U.S. Application Data

(60) Provisional application No. 62/888,059, filed on Aug. 16, 2019.

(51) Int. Cl.
*A61B 8/12* (2006.01)
*G06T 7/11* (2017.01)

(52) U.S. Cl.
CPC .......... *A61B 8/0891* (2013.01); *A61B 8/4444* (2013.01); *A61B 8/461* (2013.01); *G06T 7/11* (2017.01); *A61B 2560/0214* (2013.01); *G06T 2207/30008* (2013.01); *G06T 2207/30101* (2013.01)

(56) References Cited

U.S. PATENT DOCUMENTS

| | | | | |
|---|---|---|---|---|
| 2003/0135115 | A1* | 7/2003 | Burdette | A61N 5/103 600/437 |
| 2004/0267121 | A1 | 12/2004 | Sarvazyan | |
| 2006/0177641 | A1 | 8/2006 | Breese | |
| 2006/0184029 | A1 | 8/2006 | Haim | |
| 2007/0073155 | A1 | 3/2007 | Park | |
| 2007/0078346 | A1 | 4/2007 | Park | |
| 2009/0030339 | A1 | 1/2009 | Cheng | |
| 2013/0053687 | A1 | 2/2013 | Lin | |
| 2013/0116548 | A1 | 5/2013 | Dinesh | |
| 2014/0303662 | A1 | 10/2014 | Aoyagi | |
| 2014/0330124 | A1 | 11/2014 | Carol | |
| 2016/0317119 | A1 | 11/2016 | Tahmasebi | |
| 2017/0188990 | A1 | 7/2017 | Allmen | |
| 2019/0159753 | A1 | 5/2019 | Hsu | |

FOREIGN PATENT DOCUMENTS

| | | | |
|---|---|---|---|
| JP | 2008539932 | A | 11/2008 |
| JP | 2011104194 | A | 6/2011 |
| JP | 2012035010 | A | 5/2012 |
| JP | 2013511355 | A | 4/2013 |
| WO | 2017024576 | A1 | 2/2017 |
| WO | 2018118362 | A1 | 6/2018 |
| WO | 2018187438 | A1 | 10/2018 |

* cited by examiner

SYSTEMS AND METHODS FOR PORTABLE ULTRASOUND GUIDED CANNULATION

CROSS-REFERENCE TO RELATED APPLICATIONS

This application is a divisional of U.S. application Ser. No. 16,995,637, filed on Aug. 17, 2020, which application claims the benefit of U.S. Provisional Patent Application Ser. No. 62/888,059 filed on Aug. 16, 2019, and entitled "Semi-automated portable vascular cannulation system," which applications are incorporated herein by reference in their entireties.

STATEMENT REGARDING FEDERALLY SPONSORED RESEARCH

This invention was made with government support under FA8702-15-D-0001 awarded by the U.S. Army and Defense Health Agency. The government has certain rights in the invention.

BACKGROUND

Insertion of catheters into blood vessels, veins, or arteries can be a difficult task for non-experts or in trauma applications because the vein or artery may be located deep within the body, may be difficult to access in a particular patient, or may be obscured by trauma in the surrounding region to the vessel. Multiple attempts at penetration may result in extreme discomfort to the patient, loss of valuable time during emergency situations, or in further trauma. Furthermore, central veins and arteries are often in close proximity to each other. While attempting to access the internal jugular vein, for example, the carotid artery may instead be punctured, resulting in severe complications or even mortality due to consequent blood loss due to the high pressure of the blood flowing in the artery. Associated nerve pathways may also be found in close proximity to a vessel, such as the femoral nerve located nearby the femoral artery, puncture of which may cause significant pain or loss of function for a patient.

To prevent complications during cannulation, ultrasonic instruments can be used to determine the location and direction of the vessel to be penetrated. One method for such ultrasound guided cannulation involves a human expert who manually interprets ultrasound imagery and inserts a needle. Such a manual procedure works well only for experts who perform the procedure regularly so that they may accurately cannulate a vessel.

Systems have been developed in an attempt to remove or mitigate the burden on the expert, such as robotic systems that use a robotic arm to insert a needle. These table-top systems and robotic arms are too large for portable use, such that they may not be implemented by medics at a point of injury. In addition, these systems are limited to peripheral venous access, and may not be used to cannulate more challenging vessels or veins.

Still other systems have been used to display an image overlay on the skin to indicate where a vessel may be located, or otherwise highlight where the peripheral vein is located just below the surface. However, in the same manner as above, these systems are limited to peripheral veins, and provide no depth information that may be used by a non-expert to guide cannulation, not to mention failures or challenges associated with improper registration.

Therefore, there is a need for techniques for improved cannulation of blood vessels that is less cumbersome, more accurate, and able to be deployed by a non-expert.

SUMMARY OF THE DISCLOSURE

The present disclosure addresses the aforementioned drawbacks by providing new systems and methods for guided vascular cannulation. The systems and methods provide for image analysis to provide for segmentation of vessels of interest from image data. The image analysis provides guidance for insertion of a cannulation system into a subject and may be accomplished by a non-expert based upon the guidance provided. The guidance may include an indicator or a mechanical guide to guide a user when inserting the vascular cannulation system into a subject to penetrate the vessel of interest.

In one configuration, a system is provided for guiding an interventional device in an interventional procedure of a subject. The system includes an ultrasound probe and a guide system coupled to the ultrasound probe in a fixed position configured to guide the interventional device into a field of view (FOV) of the ultrasound probe. The system also includes a non-transitory memory having instructions stored thereon and a processor configured to access the non-transitory memory to execute the instructions. The processor is thereby caused to: access image data acquired from the subject using the ultrasound probe that includes a location of the target structure within the subject; determine an insertion point location for the interventional device based upon the location of the target structure and guide placement of the ultrasound probe to position the guide system at the insertion point location; and track the interventional device from the insertion point location to the target structure.

In another configuration, a system is provided for guiding an interventional device in an interventional procedure of a subject. The system includes a computer system configured to: access image data acquired from the subject using an ultrasound probe that includes at least one image of a target structure of the subject; determine from the image data a location of the target structure within the subject; and determine an insertion point location for the interventional device based upon the location of the target structure and guide placement of the ultrasound probe to position the guide system at the insertion point location. The system also includes an ultrasound probe and a guide system coupled to the ultrasound probe in a fixed position configured to receive and guide the interventional device into a field of view (FOV) of the ultrasound probe. The system also includes a display configured to guide the interventional device from the insertion point location to the target structure.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention. Like reference numerals will be used to refer to like parts from Figure to Figure in the following description.

DETAILED DESCRIPTION

Figure 1:
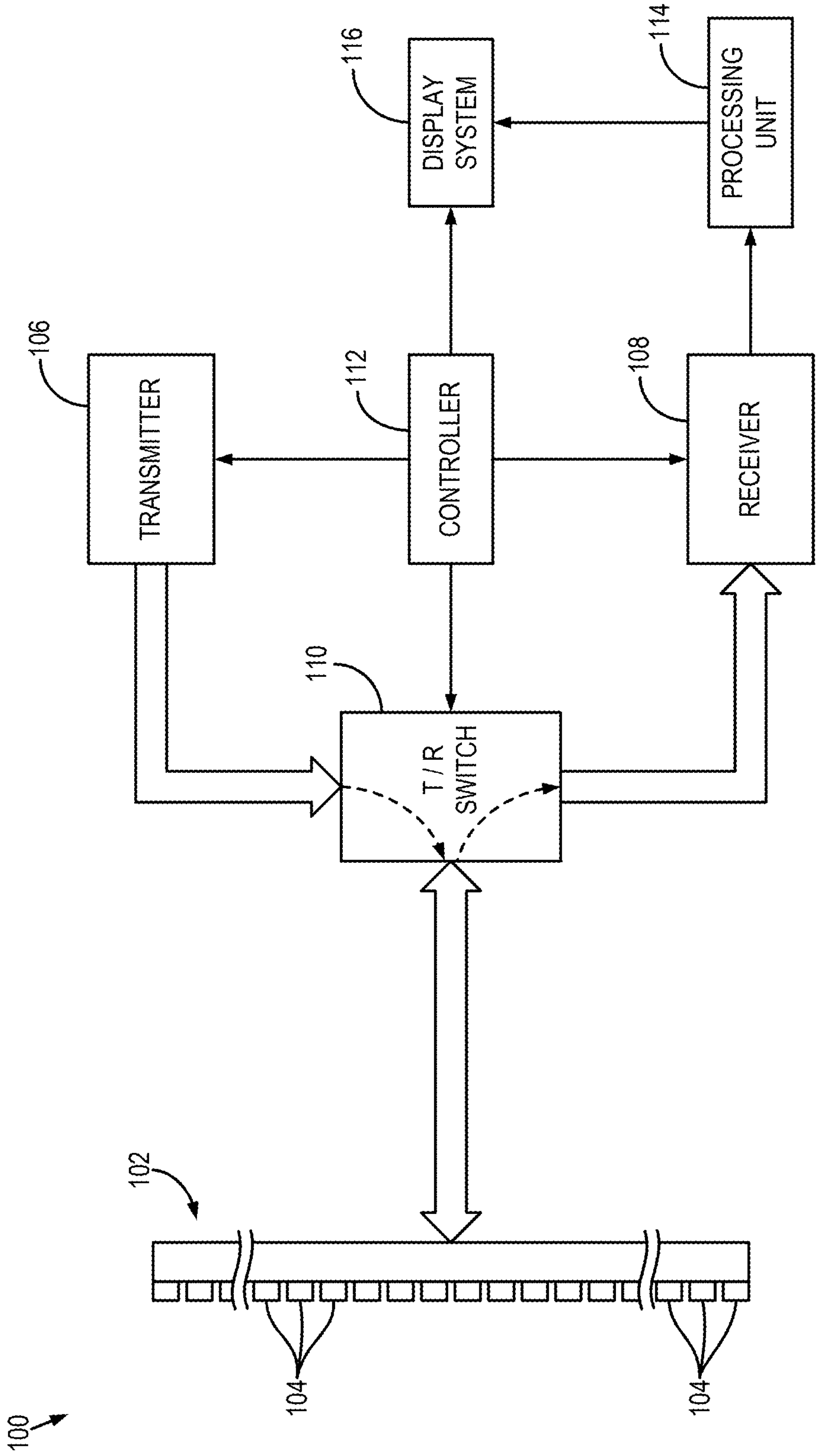
FIG. 1 is a schematic diagram of a non-limiting example ultrasound system that can implement the systems and methods described in the present disclosure.

FIG. 1 illustrates an example of an ultrasound system 100 that can implement the methods described in the present disclosure. The ultrasound system 100 includes a transducer array 102 that includes a plurality of separately driven transducer elements 104. The transducer array 102 can include any suitable ultrasound transducer array, including linear arrays, curved arrays, phased arrays, and so on. Similarly, the transducer array 102 can include a 1D transducer, a 1.5D transducer, a 1.75D transducer, a 2D transducer, a 3D transducer, and so on.

When energized by a transmitter 106, a given transducer element 104 produces a burst of ultrasonic energy. The ultrasonic energy reflected back to the transducer array 102 (e.g., an echo) from the object or subject under study is converted to an electrical signal (e.g., an echo signal) by each transducer element 104 and can be applied separately to a receiver 108 through a set of switches 110. The transmitter 106, receiver 108, and switches 110 are operated under the control of a controller 112, which may include one or more processors. As one example, the controller 112 can include a computer system.

The transmitter 106 can be programmed to transmit unfocused or focused ultrasound waves. In some configurations, the transmitter 106 can also be programmed to transmit diverged waves, spherical waves, cylindrical waves, plane waves, or combinations thereof. Furthermore, the transmitter 106 can be programmed to transmit spatially or temporally encoded pulses.

The receiver 108 can be programmed to implement a suitable detection sequence for the imaging task at hand. In some embodiments, the detection sequence can include one or more of line-by-line scanning, compounding plane wave imaging, synthetic aperture imaging, and compounding diverging beam imaging.

In some configurations, the transmitter 106 and the receiver 108 can be programmed to implement a high frame rate. For instance, a frame rate associated with an acquisition pulse repetition frequency ("PRF") of at least 100 Hz can be implemented. In some configurations, the ultrasound system 100 can sample and store at least one hundred ensembles of echo signals in the temporal direction.

The controller 112 can be programmed to implement an imaging sequence using the techniques described in the present disclosure, or as otherwise known in the art. In some embodiments, the controller 112 receives user inputs defining various factors used in the design of the imaging sequence.

A scan can be performed by setting the switches 110 to their transmit position, thereby directing the transmitter 106 to be turned on momentarily to energize transducer elements 104 during a single transmission event according to the implemented imaging sequence. The switches 110 can then be set to their receive position and the subsequent echo signals produced by the transducer elements 104 in response to one or more detected echoes are measured and applied to the receiver 108. The separate echo signals from the transducer elements 104 can be combined in the receiver 108 to produce a single echo signal.

The echo signals are communicated to a processing unit 114, which may be implemented by a hardware processor and memory, to process echo signals or images generated from echo signals. As an example, the processing unit 114 can guide cannulation of a vessel of interest using the methods described in the present disclosure. Images produced from the echo signals by the processing unit 114 can be displayed on a display system 116.

In some configurations, a non-limiting example method may be deployed on an imaging system, such as a commercially available imaging system, to provide for a portable ultrasound system with vessel cannulation guidance. The method may locate a vessel of interest, such as a vein or an artery as a user or medic moves an ultrasound probe. The system and method may provide real-time guidance to the user to position the ultrasound probe to the optimal needle insertion point. The probe may include one or more of a fixed needle guide device, an adjustable mechanical needle guide, a displayed-image needle guide, and the like. An adjustable guide may include adjustable angle and/or depth. The system may guide, or communicate placement or adjustments for the guide for the needle. The system may also regulate the needle insertion distance based upon the depth computed for the vessel of interest. The user may then insert a needle through the mechanical guide attached to the probe or displayed guide projected from the probe in order to ensure proper insertion. During needle insertion, the system may proceed to track the target blood vessel and the needle until the vessel is penetrated. A graphical user interface may be used to allow the medic to specify the desired blood vessel and to provide feedback to the medic throughout the process.

For the purposes of this disclosure and accompanying claims, the term "real time" or related terms are used to refer to and defined a real-time performance of a system, which is understood as performance that is subject to operational deadlines from a given event to a system's response to that event. For example, a real-time extraction of data and/or displaying of such data based on acquired ultrasound data may be one triggered and/or executed simultaneously with and without interruption of a signal-acquisition procedure.

In some configurations, the system may automate all ultrasound image interpretation and insertion computations, while a medic or a user may implement steps that require dexterity, such as moving the probe and inserting the needle. Division of labor in this manner may avoid using a dexterous robot arm and may result in a small system that incorporates any needed medical expertise.

Figure 2:
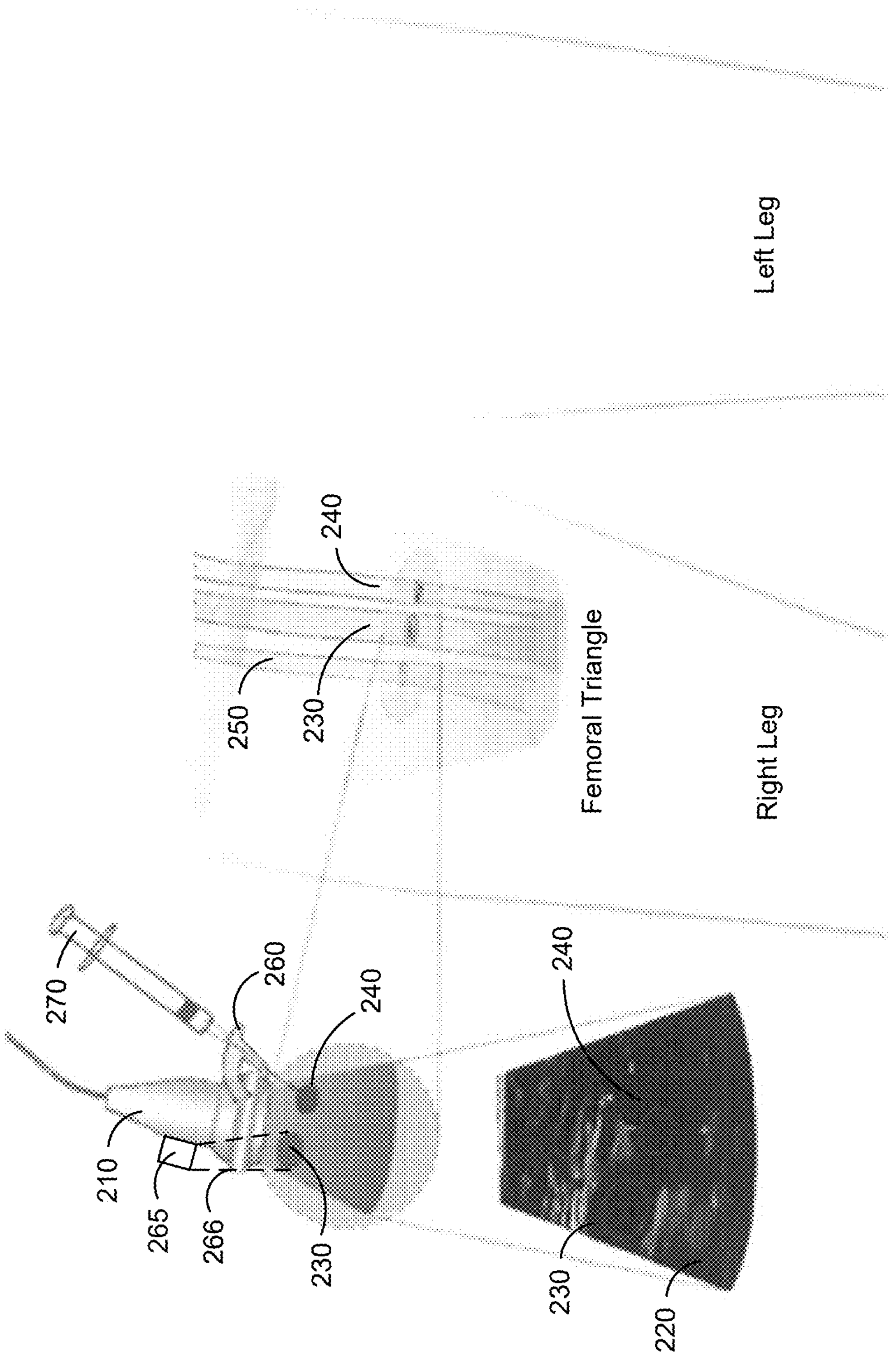
FIG. 2 is a schematic diagram of a non-limiting example configuration for guiding needle insertion into a vessel of interest using an ultrasound probe.

Referring to FIG. 2, a diagram is shown depicting a non-limiting example embodiment for guiding needle insertion into a femoral artery 230 or femoral vein 240. An ultrasound probe 210 is used to acquire an image 220 of a region of interest that includes a portion of the femoral artery 230, femoral vein 240 and other objects of interest such as femoral nerve 250. The locations of the femoral artery 230, femoral vein 240, and femoral nerve 250 may be annotated on the image 220. A mechanical needle guide 260 may be included to guide a needle 270 to penetrate the vessel of interest, such as femoral vein 240 as shown. In some configurations, visual needle guide 265 may be included where a penetration guide image 266 is projected onto the surface of a subject to guide a needle 270 to penetrate the vessel of interest, such as to femoral artery 230 as shown. Penetration guide image 266 may reflect the actual size or depth of the vessel of interest for penetration when projected onto the subject, or may provide other indicators such as measurements or a point target for penetration, and the like.

The vessels of interest may include a femoral artery, femoral vein, jugular vein, peripheral veins, subclavian vein, and or other vessels or non-vessel structures. Non-limiting example applications may include aiding a medic in performing additional emergency needle insertion procedures, such as needle decompression for tension pneumothorax (collapsed lung) and needle cricothyrotomy (to provide airway access). Portable ultrasound may be used to detect tension pneumothorax and needle insertion point (in an intercostal space, between ribs) or to detect the cricothyroid membrane and needle insertion point.

Figure 3:
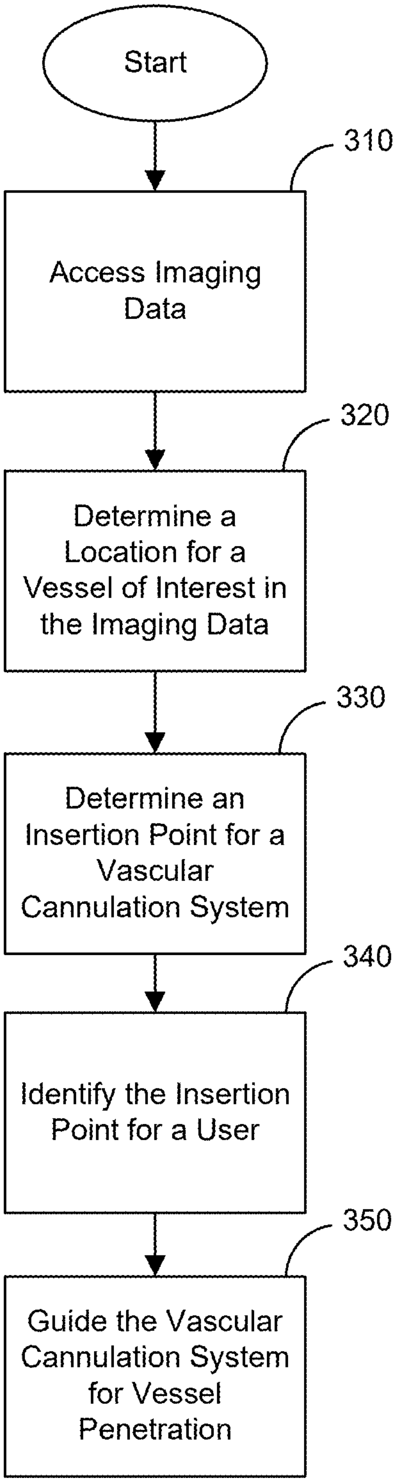
FIG. 3 is a flowchart of non-limiting example steps for a method of operating a system for guiding vascular cannulation.

Referring to FIG. 3, provides non-limiting example steps of a method of operating a system for guiding vascular cannulation. At step 310, imaging data is accessed. This may be achieved by performing an imaging acquisition and/or accessing pre-acquired image data. Imaging data may include ultrasound data, and/or may include any other form of medical imaging data, such as magnetic resonance imaging (MRI), computed tomography (CT), PET, SPECT, fluoroscopy, and the like. Using the imaging data, a vessel of interest may be determined at step 320. The location may be determined by segmenting the vessels of interest in the imaging data. Vessels of interest may include a femoral artery, femoral vein, jugular vein, peripheral veins, subclavian vein, and the like. An insertion point may then be determined at step 330 for a vascular cannulation system. Determining the insertion point may be based upon the determined location for the vessel of interest and calculating a depth and a pathway for the cannulation system from the surface of a subject to the vessel of interest without the cannulation system penetrating other organs of interest, such as a nerve. The insertion point may be determined for a user at step 340. The insertion point may be identified by illuminating a portion of the surface of a subject, or by adjusting a mechanical needle guide to the appropriate settings for the user, and the like. Depth of the needle penetration may also be controlled by a setting or a height of the mechanical guide. The vascular cannulation system may be guided to the vessel of interest for vessel penetration at step 350. Guiding the vascular cannulation system may include acquiring images of the vessel of interest and the vascular cannulation system as the cannulation system is inserted into the subject and displaying the tracked images for the user.

Figure 4A:
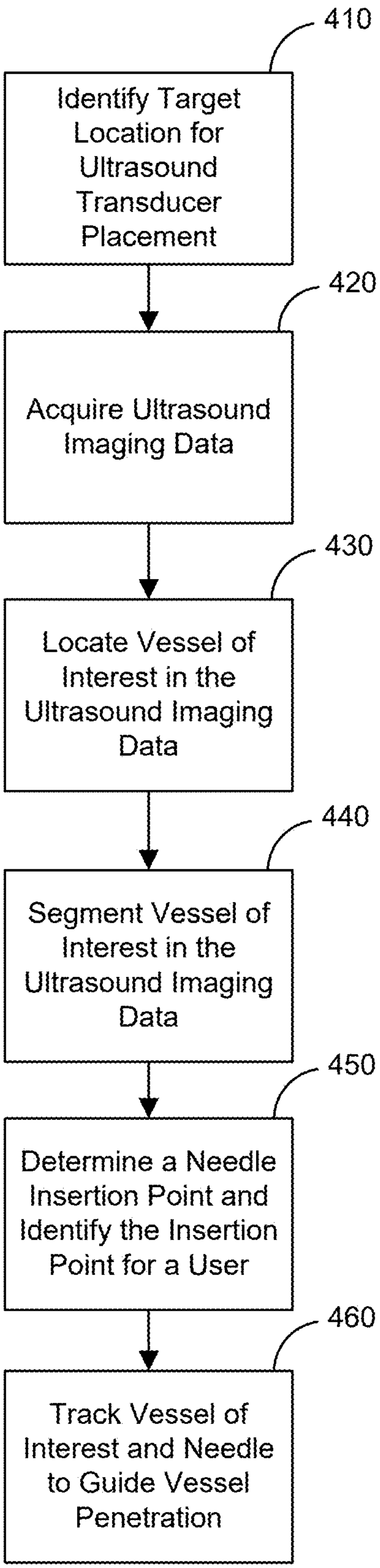
FIG. 4A is another flowchart of non-limiting example steps for a method of operating a system for guiding vascular cannulation.

Referring to FIG. 4A, non-limiting example steps are shown in another flowchart setting forth a method of guiding vascular cannulation. A target location for ultrasound transducer placement is identified by the system as having been reached at step 410. Ultrasound imaging data is acquired at step 420 from the target location. A location for a vessel of interest in the imaging data is determined at step 430. Vessels of interest are segmented in the ultrasound imaging data at step 440. An insertion point may then be determined at step 450 for a needle. Determining the insertion point may be based upon the determined and segmented location for the vessel of interest. In some configurations, the method includes calculating a depth and a pathway from the surface of a subject to the vessel of interest without the needle penetrating other organs or structures of interest along the pathway, such as a nerve. The insertion point may also be identified for a user at step 450. As above, the insertion point may be identified by illuminating a portion of the surface of a subject, by ensuring a fixed needle guide is placed over the insertion point, or by automatically adjusting an adjustable mechanical needle guide to the appropriate settings for the user, and the like. Depth of the needle penetration may also be controlled by an adjusted setting for the adjustable mechanical guide, or a fixed height of the fixed guide. The needle may be tracked and guided to the vessel of interest for vessel penetration at step 460. Guiding the needle may include acquiring ultrasound images of the vessel of interest and the needle as the needle is inserted into the subject and displaying the tracked images for the user.

Any ultrasound probe may be used in accordance with the present disclosure, including 1D, 2D, linear, phased array, and the like. In some configurations, an image is displayed for a user of the vessel of interest with any tracking information for the needle overlaid on the image. In some configurations, no image is displayed for a user and instead only the insertion point may be identified by illuminating a portion of the surface of a subject. In some configurations, no image is displayed and the user is only informed of the probe reaching the proper location whereby a mechanical needle guide is automatically adjusted to the appropriate settings, such as angle and/or depth to target a vessel of interest. The user may be informed of the probe reaching the proper location by any appropriate means, such as light indicator, a vibration of the probe, and the like.

In some configurations, identification of placement of the ultrasound transducer at a target location may be performed automatically by the system at step 410. Image data may be used for identifying anatomy, such as a femoral triangle, jugular region, and the like, and may be accessed by the system to provide automatic identification for where the ultrasound transducer has been placed. In some configurations, a user may specify the vessel of interest to be targeted, such as whether to target an artery or a vein. In a non-limiting example combination of the configurations, the location of the ultrasound transducer on the subject may be automatically determined along with the anatomy being imaged, with the user specifying the vessel of interest to target in the automatically identified anatomy. A minimum of user input may be used in order to mitigate the time burden on a user.

Segmenting the vessels of interest at step 440 may be based on machine learning of morphological and spatial information in the ultrasound images. In some configurations, a neural network may be deployed for machine learning and may learn features at multiple spatial and temporal scales. Vessels of interest may be distinguished based on shape and/or appearance of the vessel wall, shape and/or appearance of surrounding tissues, and the like. In a non-limiting example, stiffer walls and a circular shape may be used to distinguish an artery in an image, whereas an ellipsoidal shape may be used to identify a vein. Real-time vessel segmentation may be enabled by a temporally trained routine without a need for conventional post-hoc processing.

Temporal information may be used with segmenting the vessels of interest at step 440. Vessel appearances and shape may change with movement of the anatomy over time, such as changes with heartbeat, or differences in appearance between hypotensive and normal-tensile situations. Machine learning routines may be trained with data from multiple time periods with differences in anatomy being reflected over the different periods of time. With a temporally trained machine learning routine, vessel segmentation may be performed in a robust manner over time for a subject without misclassification and without a need to find a specific time frame or a specific probe position to identify vessels of interest.

In some configurations, to prevent any potential misclassifications conflicting information checks may be included in the system. A conflicting information check may include taking into consideration the general configuration of the anatomy at the location of the probe. In a non-limiting example, if the system initially identifies two arteries at a location of the probe, but the general anatomy at the location of the probe indicates that an artery and a vein should be returned as results instead, then the system will automatically correct to properly identify an artery and a vein instead of the mistaken two arteries to prevent a misclassification.

Identifying an insertion point for a user at step 450 may also include where the system automatically takes into account the orientation of the probe on a body. A conventional ultrasound probe includes markings on the probe to indicate the right vs left side of probe, which allows a user to orient a probe such that the mark is on the right of the patient, for example. The probe orientation may be also be determined from an analysis of the acquired ultrasound images, or monitoring of the orientation of the markings, such as by an external camera. In some configurations, the needle guide attachment may be configured fit into the markings on the probe to ensure that the device is consistent with the orientation of the probe.

A safety check may also be performed as part of determining an insertion point at step 450 for a needle. A safety check may include confirming that there are no critical structures, such as a bone, an unintended blood vessel, a non-target organ, a nerve, and the like, intervening on the needle's path to penetrate the vessel. The safety check may also include forcing the system to change the location of the penetration to avoid penetrating such critical structures. In some configurations, the safety check may include confirming the needle has penetrated the vessel of interest by the tracking and guidance at step 460. The safety check may also include determining that the user is holding the system in a stable position, by verifying from the ultrasound image or from an inertial measurement unit on the handle of the system.

Figure 4B:
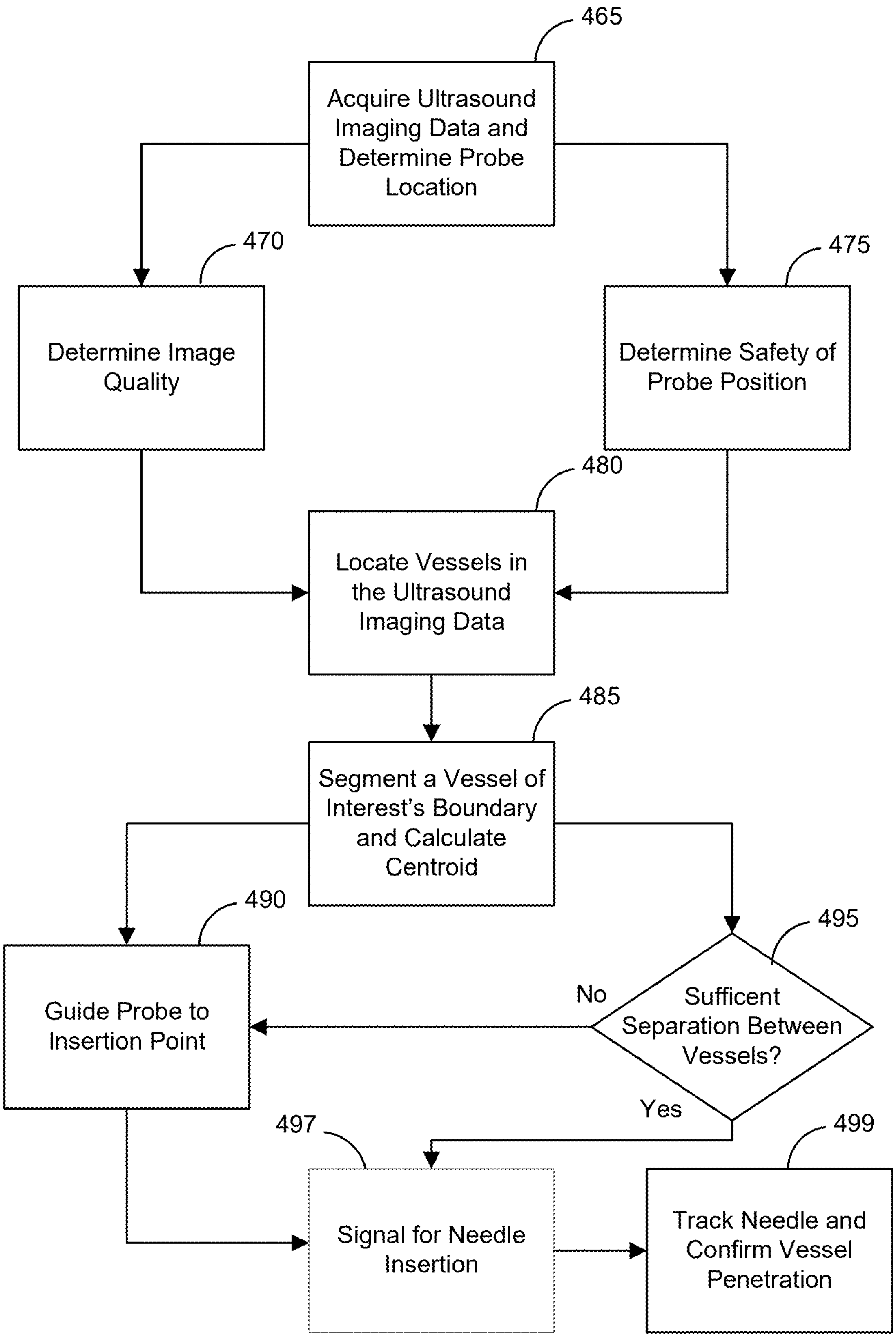
FIG. 4B is a flowchart of non-limiting example steps for a method of guiding needle penetration of a vessel of interest.

Referring to FIG. 4B, non-limiting example steps are shown in a flowchart setting forth a method of guiding needle penetration of a vessel of interest. Ultrasound imaging data is acquired and a probe location is determined at step 465. An image quality may be determined at step 470, and the safety of the probe location for penetrating a vessel in the subject may be determined at step 475. Vessels may be located in the imaging data at step 480. A vessel of interest's boundary may be segmented and a centroid calculated for the vessel of interest at step 485. The probe may be guided to an insertion point at step 490. Sufficient separation between vessels may be determined or confirmed at step 495. If there is not sufficient separation, the probe may be guided to a new insertion position at step 490. If there is sufficient separation, then a signal may be provided to a user to proceed with needle insertion at step 497. Such a signal may be provided on a graphical user interface, or a light in the probe, and the like. The needle may be tracked and vessel penetration confirmed at step 499.

In some configurations, the method includes guiding a user in placement of the ultrasound probe on the subject. A target for penetration may be identified, such as by machine learning in accordance with the present disclosure, and localized. A user may then be guided in which direction to move the ultrasound probe for placement over an identified target. Once the ultrasound probe has reached the target location, a signal may indicate for the user to stop moving the probe. Guidance may be provided by the signal, such as the light on the probe, in a non-limiting example. Needle placement and penetration may proceed after the location of the target has been reached.

Figure 5:
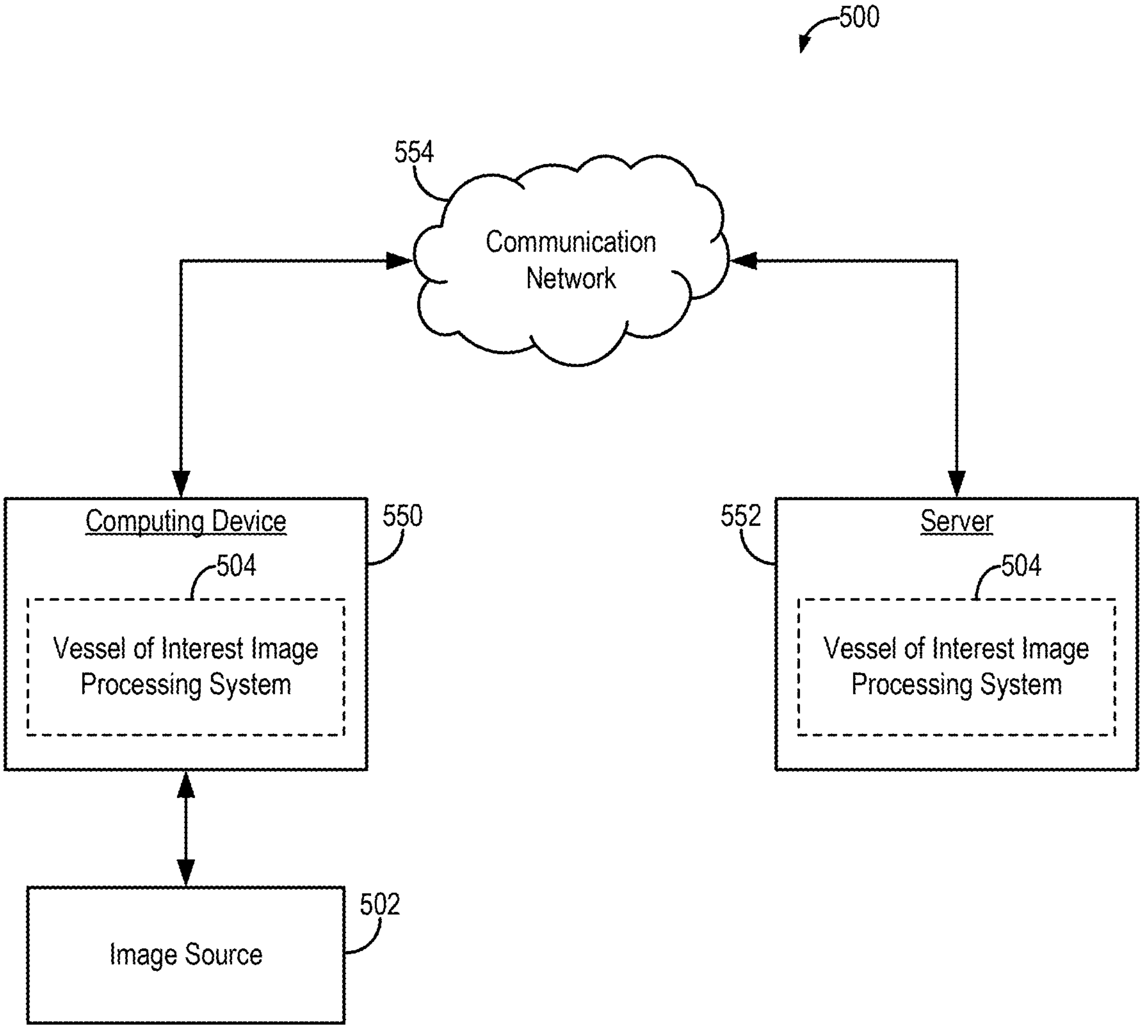
FIG. 5 is a block diagram of an example system that can implement a vessel of interest image processing system for generating images of a vessel of interest or otherwise measuring or predicting a location for a vessel of interest using a hybrid machine learning and mechanistic model.

Referring to FIG. 5, an example of a system 500 for generating and implementing a hybrid machine learning and mechanistic model in accordance with some embodiments of the systems and methods described in the present disclosure is shown. As shown in FIG. 5, a computing device 550 can receive one or more types of data (e.g., ultrasound, multiparametric MRI data, vessel of interest image data, and the like) from image source 502. In some embodiments, computing device 550 can execute at least a portion of a vessel of interest image processing system 504 to generate images of a vessel of interest, or otherwise segment a vessel of interest from data received from the image source 502.

Additionally or alternatively, in some embodiments, the computing device 550 can communicate information about data received from the image source 502 to a server 552 over a communication network 554, which can execute at least a portion of the vessel of interest image processing system 504 to generate images of a vessel of interest, or otherwise segment a vessel of interest from data received from the image source 502. In such embodiments, the server 552 can return information to the computing device 550 (and/or any other suitable computing device) indicative of an output of the vessel of interest image processing system 504 to generate images of a vessel of interest, or otherwise segment a vessel of interest from data received from the image source 502.

In some embodiments, computing device 550 and/or server 552 can be any suitable computing device or combination of devices, such as a desktop computer, a laptop computer, a smartphone, a tablet computer, a wearable computer, a server computer, a virtual machine being executed by a physical computing device, and so on. The computing device 550 and/or server 552 can also reconstruct images from the data.

In some embodiments, image source 502 can be any suitable source of image data (e.g., measurement data, images reconstructed from measurement data), such as an ultrasound system, another computing device (e.g., a server storing image data), and so on. In some embodiments, image source 502 can be local to computing device 550. For example, image source 502 can be incorporated with computing device 550 (e.g., computing device 550 can be configured as part of a device for capturing, scanning, and/or storing images). As another example, image source 502 can be connected to computing device 550 by a cable, a direct wireless link, and so on. Additionally or alternatively, in some embodiments, image source 502 can be located locally and/or remotely from computing device 550, and can communicate data to computing device 550 (and/or server 552) via a communication network (e.g., communication network 554).

In some embodiments, communication network 554 can be any suitable communication network or combination of communication networks. For example, communication network 554 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 5 can each be any suitable communications link or combination of communications links, such as wired links, fiber optic links, Wi-Fi links, Bluetooth links, cellular links, and so on.

Figure 6:
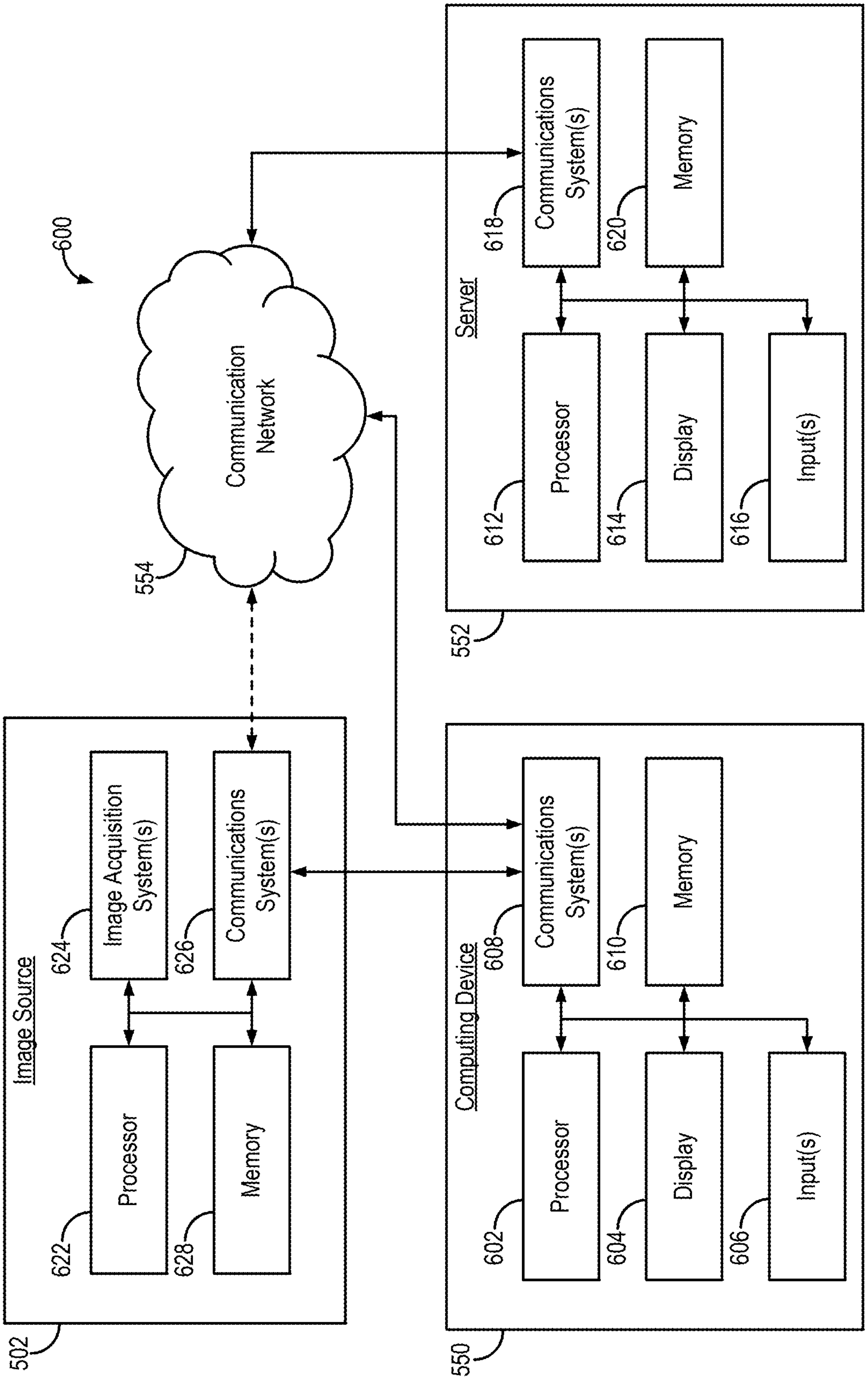
FIG. 6 is a block diagram of example hardware components of the system of FIG. 5.

Referring now to FIG. 6, an example of hardware 600 that can be used to implement image source 502, computing device 550, and server 554 in accordance with some embodiments of the systems and methods described in the present disclosure is shown. As shown in FIG. 6, in some embodiments, computing device 550 can include a processor 602, a display 604, one or more inputs 606, one or more communication systems 608, and/or memory 610. In some embodiments, processor 602 can be any suitable hardware processor or combination of processors, such as a central processing unit ("CPU"), a graphics processing unit ("GPU"), and so on. In some embodiments, display 604 can include any suitable display devices, such as a computer monitor, a touchscreen, a television, and so on. In some embodiments, inputs 606 can include any suitable input devices and/or sensors that can be used to receive user input, such as a keyboard, a mouse, a touchscreen, a microphone, and so on.

In some embodiments, communications systems 608 can include any suitable hardware, firmware, and/or software for communicating information over communication network 554 and/or any other suitable communication networks. For example, communications systems 608 can include one or more transceivers, one or more communication chips and/or chip sets, and so on. In a more particular example, communications systems 608 can include hardware, firmware and/or software that can be used to establish a Wi-Fi connection, a Bluetooth connection, a cellular connection, an Ethernet connection, and so on.

In some embodiments, memory 610 can include any suitable storage device or devices that can be used to store instructions, values, data, or the like, that can be used, for example, by processor 602 to present content using display 604, to communicate with server 552 via communications system(s) 608, and so on. Memory 610 can include any suitable volatile memory, non-volatile memory, storage, or any suitable combination thereof. For example, memory 610 can include RAM, ROM, EEPROM, one or more flash drives, one or more hard disks, one or more solid state drives, one or more optical drives, and so on. In some embodiments, memory 610 can have encoded thereon, or otherwise stored therein, a computer program for controlling operation of computing device 550. In such embodiments, processor 602 can execute at least a portion of the computer program to present content (e.g., images, user interfaces, graphics, tables), receive content from server 552, transmit information to server 552, and so on.

In some embodiments, server 552 can include a processor 612, a display 614, one or more inputs 616, one or more communications systems 618, and/or memory 620. In some embodiments, processor 612 can be any suitable hardware processor or combination of processors, such as a CPU, a GPU, and so on. In some embodiments, display 614 can include any suitable display devices, such as a computer monitor, a touchscreen, a television, and so on. In some embodiments, inputs 616 can include any suitable input devices and/or sensors that can be used to receive user input, such as a keyboard, a mouse, a touchscreen, a microphone, and so on.

In some embodiments, communications systems 618 can include any suitable hardware, firmware, and/or software for communicating information over communication network 554 and/or any other suitable communication networks. For example, communications systems 618 can include one or more transceivers, one or more communication chips and/or chip sets, and so on. In a more particular example, communications systems 618 can include hardware, firmware and/or software that can be used to establish a Wi-Fi connection, a Bluetooth connection, a cellular connection, an Ethernet connection, and so on.

In some embodiments, memory 620 can include any suitable storage device or devices that can be used to store instructions, values, data, or the like, that can be used, for example, by processor 612 to present content using display 614, to communicate with one or more computing devices 550, and so on. Memory 620 can include any suitable volatile memory, non-volatile memory, storage, or any suitable combination thereof. For example, memory 620 can include RAM, ROM, EEPROM, one or more flash drives, one or more hard disks, one or more solid state drives, one or more optical drives, and so on. In some embodiments, memory 620 can have encoded thereon a server program for controlling operation of server 552. In such embodiments, processor 612 can execute at least a portion of the server program to transmit information and/or content (e.g., data, images, a user interface) to one or more computing devices 550, receive information and/or content from one or more computing devices 550, receive instructions from one or more devices (e.g., a personal computer, a laptop computer, a tablet computer, a smartphone), and so on.

In some embodiments, image source 502 can include a processor 622, one or more image acquisition systems 624, one or more communications systems 626, and/or memory 628. In some embodiments, processor 622 can be any suitable hardware processor or combination of processors, such as a CPU, a GPU, and so on. In some embodiments, the one or more image acquisition systems 624 are generally configured to acquire data, images, or both, and can include an RF transmission and reception subsystem of an MRI system. Additionally or alternatively, in some embodiments, one or more image acquisition systems 624 can include any suitable hardware, firmware, and/or software for coupling to and/or controlling operations of an MRI system or an RF subsystem of an MRI system. In some embodiments, one or more portions of the one or more image acquisition systems 624 can be removable and/or replaceable.

Note that, although not shown, image source 502 can include any suitable inputs and/or outputs. For example, image source 502 can include input devices and/or sensors that can be used to receive user input, such as a keyboard, a mouse, a touchscreen, a microphone, a trackpad, a trackball, and so on. As another example, image source 502 can include any suitable display devices, such as a computer monitor, a touchscreen, a television, etc., one or more speakers, and so on.

In some embodiments, communications systems 626 can include any suitable hardware, firmware, and/or software for communicating information to computing device 550 (and, in some embodiments, over communication network 554 and/or any other suitable communication networks). For example, communications systems 626 can include one or more transceivers, one or more communication chips and/or chip sets, and so on. In a more particular example, communications systems 626 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 628 can include any suitable storage device or devices that can be used to store instructions, values, data, or the like, that can be used, for example, by processor 622 to control the one or more image acquisition systems 624, and/or receive data from the one or more image acquisition systems 624; to images from data; present content (e.g., images, a user interface) using a display; communicate with one or more computing devices 550; and so on. Memory 628 can include any suitable volatile memory, non-volatile memory, storage, or any suitable combination thereof. For example, memory 628 can include RAM, ROM, EEPROM, one or more flash drives, one or more hard disks, one or more solid state drives, one or more optical drives, and so on. In some embodiments, memory 628 can have encoded thereon, or otherwise stored therein, a program for controlling operation of image source 502. In such embodiments, processor 622 can execute at least a portion of the program to generate images, transmit information and/or content (e.g., data, images) to one or more computing devices 550, receive information and/or content from one or more computing devices 550, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

Figure 7A:
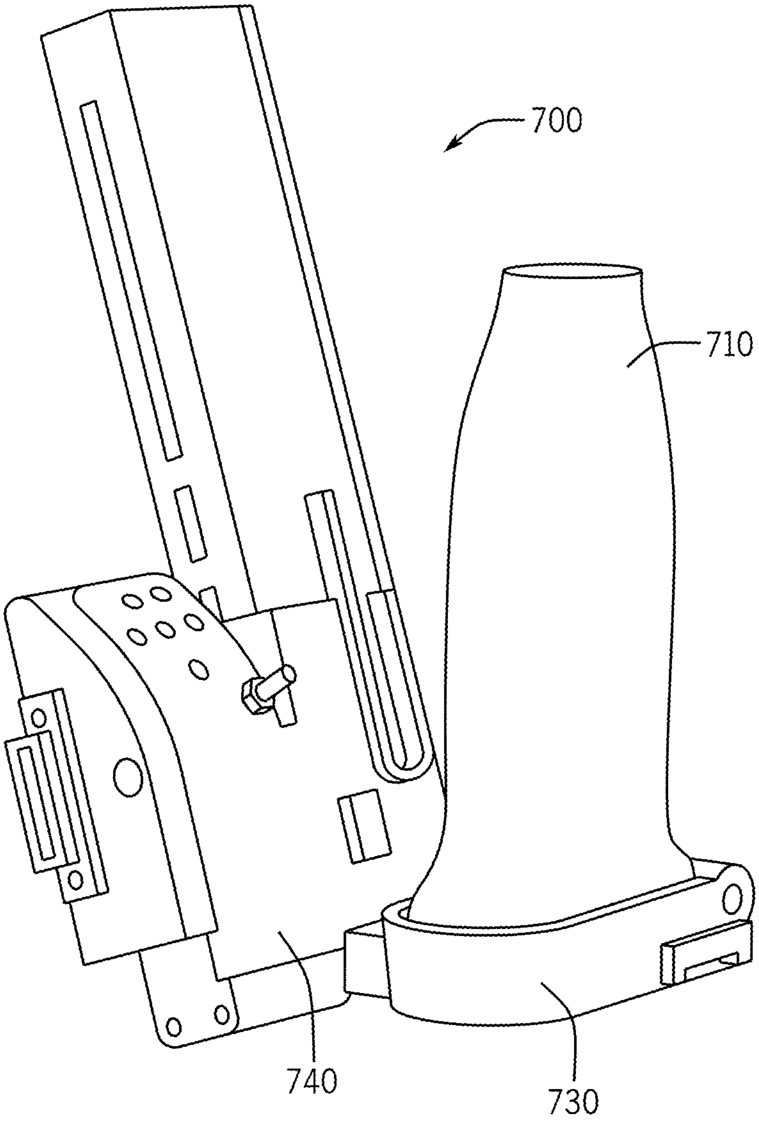
FIG. 7A is a perspective view of a non-limiting example interventional device guide coupled to an ultrasound probe.

Referring to FIG. 7A, a perspective view of a non-limiting example interventional device guide injection assembly 700 coupled to an ultrasound probe 710 is shown. Base 740 is shown with ultrasound handle fixture 730 that provides detachable coupling to ultrasound probe 710. The injection assembly 700 may be attached to any ultrasound device, such as by being strapped onto an ultrasound probe 710 using the ultrasound handle fixture 730. Base 740 may include a mechanical support resting on the skin in order to minimize kick-back and improve needle insertion accuracy.

Figure 7D:
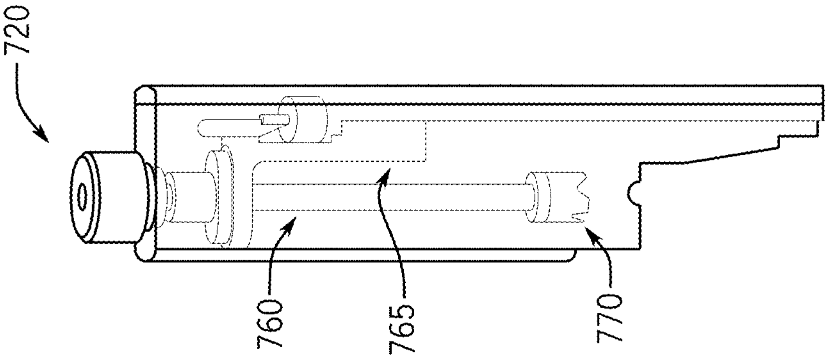
FIG. 7D is a cross-section of a non-limiting example cartridge compatible with the injection assemble of FIG. 7B.
Figure 7C:
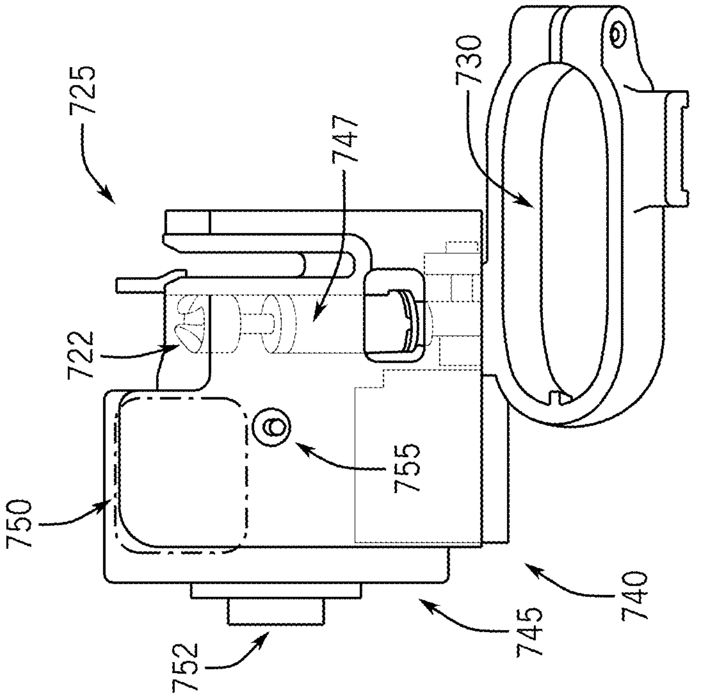
FIG. 7C is a side view of the base and ultrasound probe fixture for the interventional device guide of FIG. 7B.
Figure 7B:
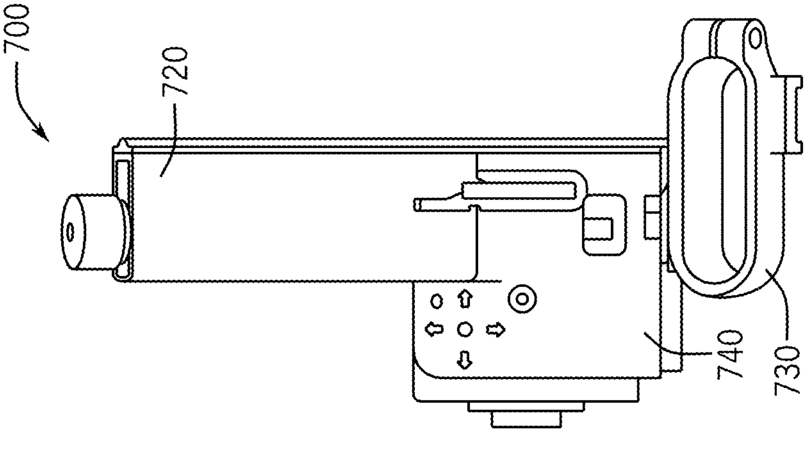
FIG. 7B is a side view of the interventional device guide of FIG. 7A.

Referring to FIG. 7B, a side view of the interventional device guide injection assembly 700 of FIG. 7A is shown. In a non-limiting example, base 740 contains a motor to set the angle at which the interventional device, which may be a needle, will be inserted. The base 740 may also contain a second drive motor to drive the interventional device to the desired depth. The motor may be controlled to vary the needle insertion speed at different insertion depths, e.g., the needle may be inserted relatively slowly through the skin to minimize kick-back and improve accuracy, and then inserted faster subsequently. In some configurations, the drive motor function may be replaced or augmented by a spring or any suitable method of storing mechanical energy, and an additional motor or other suitable method of mechanical actuation to enable injection into a subject. Cartridge 720 is detachably coupled to base 740 and may be configured for the intervention being performed. In non-limiting examples, cartridge 720 may include configurations to treat indications requiring vascular access, tension pneumothorax, or establishing of an airway. Non-limiting example cartridge configurations are listed in Table 1 below.

TABLE 1

Non-limiting example cartridge configurations

| Intervention | | Cartridge Generation | Capability |
|---|---|---|---|
| Vascular | Femoral Artery/Vein | 1 | Needle only |
| | | 2 | Needle with dilator and/or guide wire (or similarly functioning guide) |
| | | 3 | REBOA, clotting agent, other intervention |
| | Internal Jugular | 1 | Needle only |

TABLE 1-continued

Non-limiting example cartridge configurations

| | Intervention | Cartridge Generation | Capability |
|---|---|---|---|
| | Vein | 2 | Needle with dilator and/or guide wire (or similarly functioning guide) |
| | | 3 | REBOA, clotting agent, other intervention |
| Air | Cricothyrotomy (or similar methods of establishing airway access) | 1<br>2<br>3 | Needle only<br>Breathing tube<br>Breathing tube + forced air |
| | Tension Pneumothorax | 1<br>2 | Needle only<br>Chest tube |
| Abdomen | Ascites | 1<br>2 | Needle only<br>Catheter |
| | Bladder | 1 | Needle only |
| | Pregnant uterus amniocentesis | 1 | Needle only |
| Soft tissue | Focal lesion/tumor biopsy | 1 | Needle only |

Referring to FIG. 7C is a side view of the base and ultrasound probe fixture for the interventional device guide of FIG. 7B. Base 740 includes a drive motor 745 to set an insertion angle and/or depth for an interventional device held by cartridge slot 725 coupled by cartridge coupling 722. Advancement motor 747 may be included to advance an interventional device with activation by advancement control 755, which in a non-limiting example is a button. Electrical interface connector 752 may provide communication to an ultrasound imaging system or separate display system. User guidance signal 750 provide feedback to a user and may take the form or any display intending to direct the user in gross and/or precise placement of the device. In a non-limiting example, user guidance signal 750 includes an arrangement of LEDs. In some configurations, user guidance signal 750 may be coupled to the cartridge 720 and may be specific to the particular indication being treated.

Referring to FIG. 7D is a cross-section of a non-limiting example cartridge 720 compatible with the injection assembly 700 of FIG. 7B. Lead screw 760 may provide for actuation of base coupling 770 to couple the non-limiting example cartridge 720 to base 740 in FIG. 7B. Needle carriage 765 is shown as a non-limiting example of a needle cartridge application.

Figure 8A:
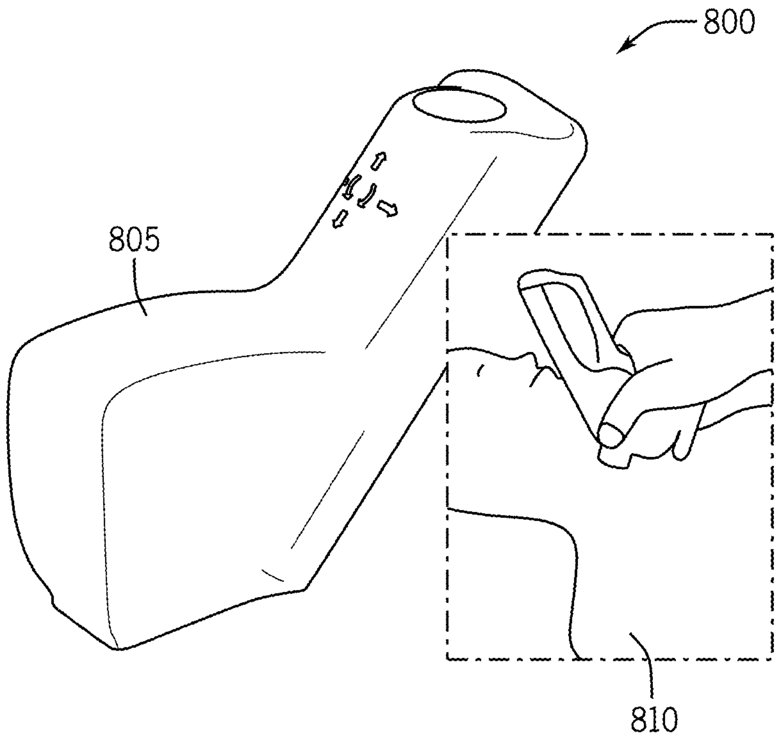
FIG. 8A is a perspective view of a non-limiting example interventional device guide integrated with an ultrasound probe.

Referring to FIG. 8A, a perspective view of a non-limiting example interventional device guide integrated with an ultrasound probe is shown. Integrated interventional device guide 800 is shown being placed on a subject 810. The integrated interventional device guide 800 may include functionality similar to injection assembly 700 described above with integration with an ultrasound probe. The integrated interventional device guide 800 may be ultrasound guided, and may employ machine learning or artificial intelligence for identifying a target structure for penetration and guiding penetration of the target structure, in accordance with the present disclosure. The integrated ultrasound transducer may provide for excitation, for reading a source, for processing ultrasound signals, and the like. Integrated interventional device guide 800, may include onboard artificial intelligence algorithms, motors, associated drive circuitry, other electronics/mechanics, and the like fit within a housing 805 for the integrated device guide 800. A cartridge, such as described herein, may be detachably coupled to integrated interventional device guide 800. In some configurations, the integrated interventional device guide 800 may be robotically controlled.

Figure 8B:
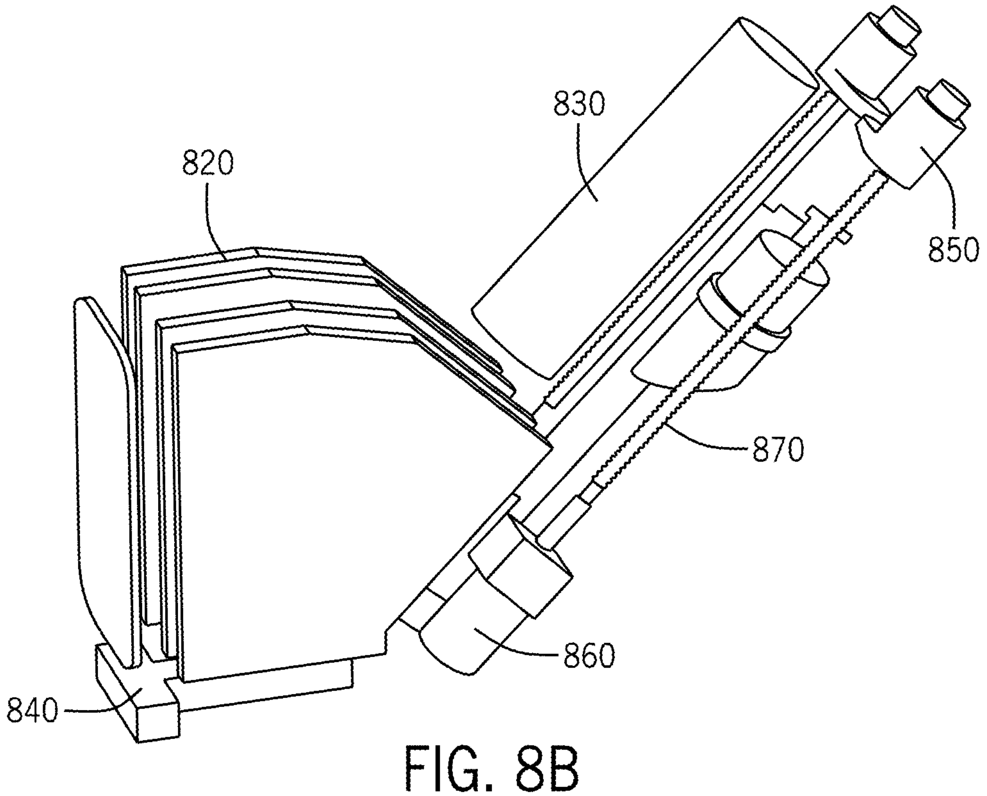
FIG. 8B is an exploded view of the integrated interventional device guide and ultrasound probe of FIG. 8A.

Referring to FIG. 8B is an exploded view of the integrated interventional device guide 800 and ultrasound probe of FIG. 8A is shown. Circuit boards 820 may provide for ultrasound guidance from ultrasound transducers 840, and may employ machine learning or artificial intelligence for identifying a target structure for penetration and guiding penetration of the target structure, in accordance with the present disclosure. Battery 830 may provide power for the integrated device. One battery cell is shown in FIG. 8B, but it is to be appreciated that any number of battery cells may be used, such as two cells for extended life, or any other form of power supply. Drivetrain 850 may provide for independent needle or interventional device insertion and cannula insertion. Needle and cannula 870 may be inserted into a subject with motors 860.

Figure 9:
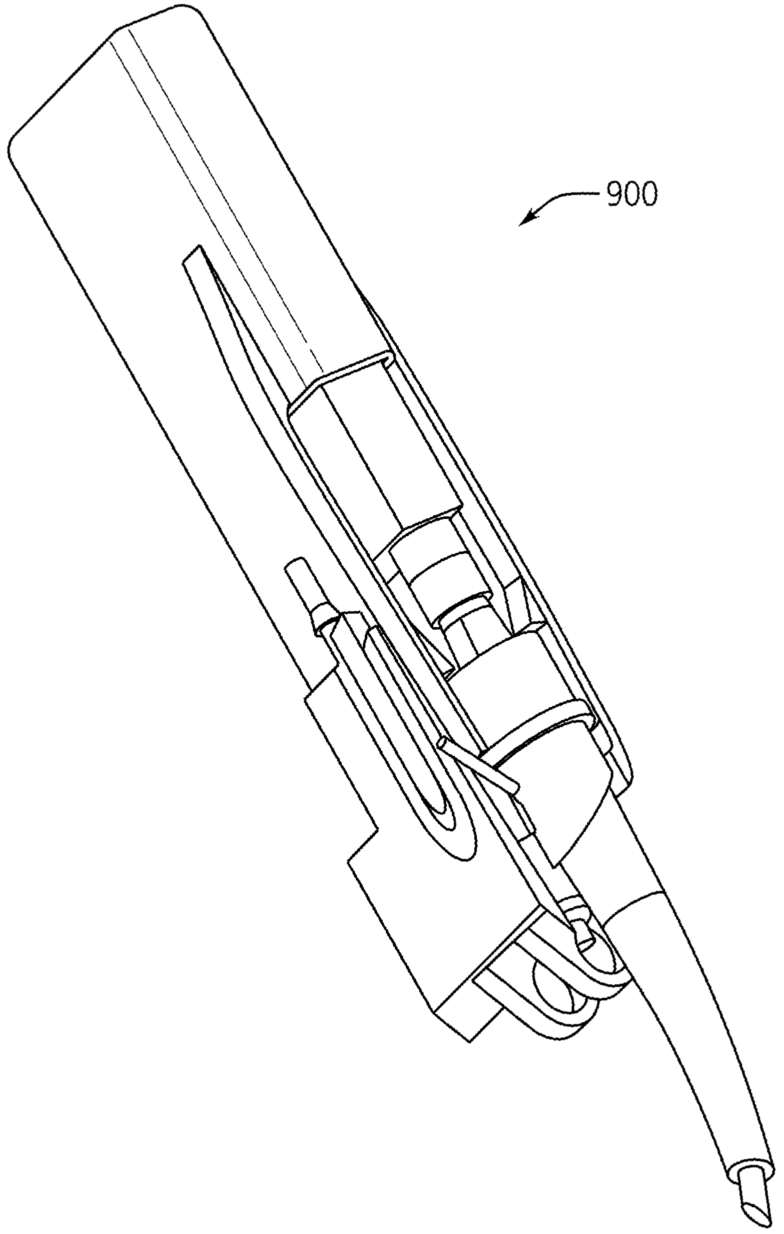
FIG. 9 is perspective view of a non-limiting example cricothyrotomy cartridge for use in accordance with the present disclosure.

Referring to FIG. 9 is perspective view of a non-limiting example cricothyrotomy cartridge 900 for use in accordance with the present disclosure. As indicated in Table 1 above, different clinical indications may require different types of needles or other hardware/drugs to be introduced into the body. In a non-limiting example, in the case of non-compressible hemorrhage, blood products may need to be rapidly introduced and a needle sheath may provide a path of adequate diameter for rapid introduction of fluid. In another non-limiting example, a catheter may need to be introduced, or a dilating element with larger lumen may be required. Each cartridge may be designed, and clearly labeled with, an intended application. In some configurations, the system may be capable of knowing which type of cartridge device is “plugged” into it. This information may be conveyed through electrical communication between the cartridge and the base, such as radio frequency or direct conducted signals, or through optical communication between the cartridge and the base, or through a mechanical keying specific to the cartridge/base assembly that indicates the cartridge type used, and the like. In a non-limiting example of a mechanical keying, the Femoral Artery/Vein Generation 1 cartridge of Table 1 could be configured such that it depresses a first button in the cartridge slot in the base, whereas the generation 2 cartridge in this family could be configured to depress a second button. In this manner, the base may distinguish between which cartridges have been inserted. In some configurations, the cartridge may be inside of the sterile surgical barrier with the base external the sterile barrier, such that communication of the cartridge type may be performed through the barrier to ensure safe, effective treatment.

Referring to FIGS. 10A-E, side views of inserting and removing a non-limiting example dilating component into a subject is shown. Some types of cartridges shown in Table 1 may require more than a single step needle insertion process. In a non-limiting example, a cartridge may be configured to install a dilated lumen, which may include a multi-step process. In a non-limiting example, installing a breathing tube through the cricothyroid membrane may include a coaxial assembly consisting of a sharp center element for puncturing and initial path guidance in addition to a coaxial element for dilation and eventual passage of air, which may be introduced according to FIGS. 10A-E.

Figure 10C:
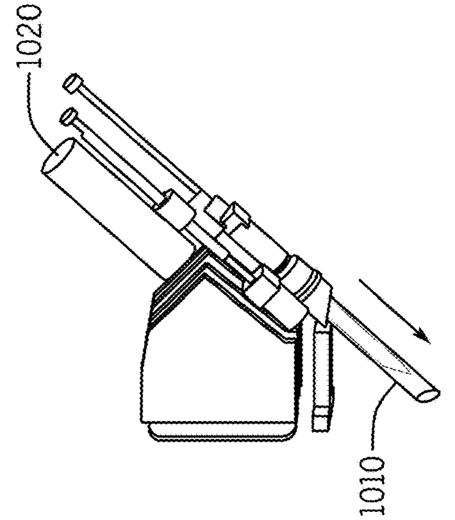
FIG. 10C is a side view of advancing the non-limiting example dilating component over the needle and into the subject.
Figure 10B:
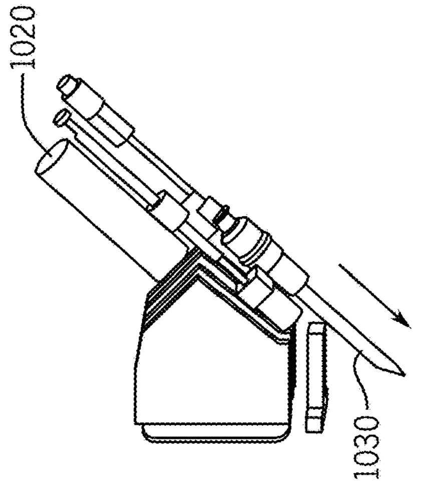
FIG. 10B is a side view of aligning the non-limiting example dilating component with the interventional device guide and advancing a needle to guide the non-limiting example dilating component into the subject.
Figure 10E:
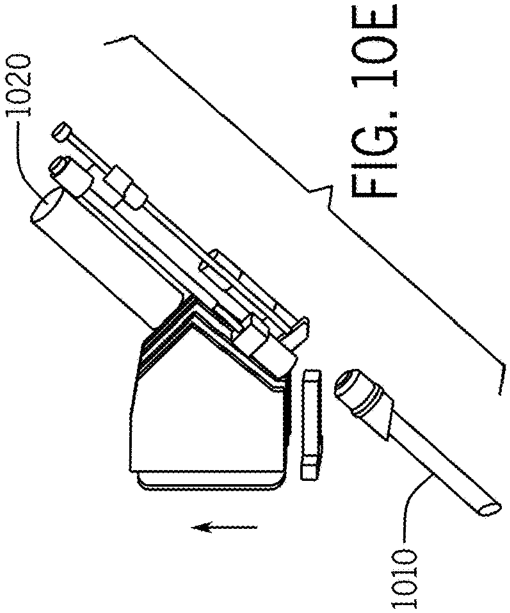
FIG. 10E is a side view of removing the interventional device guide and leaving the non-limiting example dilating component in the subject.
Figure 10A:
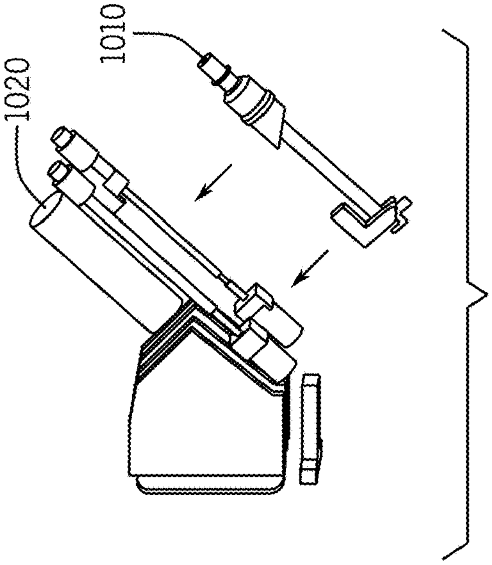
FIG. 10A is a side view of inserting a non-limiting example dilating component into the interventional device guide.

The sequence shown in FIGS. 10A-10E may be entirely automated by the motors or other mechanical actuation in the system, or may be a combination of automated actuation and human handling. Referring to FIG. 10A, a side views of inserting a non-limiting example dilating component 1010 into a subject is shown. In some configurations, a protector may be removed to insert a disposable version of the dilator 1010 to maintain sterility and safety.

Referring to FIG. 10B a side view of aligning a non-limiting example dilating component 1010 with the interventional device guide 1020 is shown. Needle 1030 may be deployed after device alignment, which may be coaxial with dilating component 1010. In some configurations, the receiving anatomy may be more sensitive to damage or additional mechanical guidance may be required for proper introduction of the larger diameter element. In such configurations, a "guide-wire" device may be used to temporarily protrude from the tip of the inserted assembly, in a function similar to that of the guide-wire used in the Seldinger technique. The "guide-wire" device may be deployed between steps depicted in FIG. 10B and FIG. 10C.

Figure 10D:
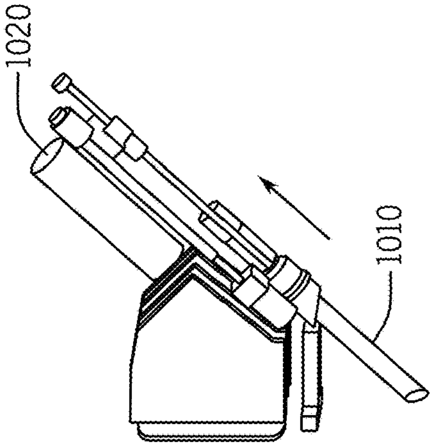
FIG. 10D is a side view of retracting the needle and leaving the non-limiting example dilating component in the subject.

Referring to FIG. 10C, a side view of advancing a non-limiting example dilating component 1010 into the subject is shown. Dilating component 1010 may be advanced over, and may be coaxial with, needle 1030. Dilating component 1010 may provide for expanded access into the subject after insertion. Referring to FIG. 10D, a side view of retracting the needle 1030 from the subject is shown. Referring to FIG. 10E, a side view of removing the interventional device guide 1020 is show where dilating component 1010 is retained in the subject and may be used for access from an interventional device.

The present disclosure has described one or more preferred embodiments, and it should be appreciated that many equivalents, alternatives, variations, and modifications, aside from those expressly stated, are possible and within the scope of the invention.

The invention claimed is:

1. A computer program product comprising one or more non-transitory computer storage media having stored thereon instructions that, when executed by one or more computing devices, cause the one or more computing devices to perform operations comprising:

accessing image data acquired from a subject using an ultrasound probe on a surface of the subject, the image data including at least one image of a target structure of the subject;

segmenting the image data based upon appearance of the target structure;

determining, from the segmented image data, a location of the target structure within the subject;

determining an insertion point location for an interventional device based upon the location of the target structure;

guiding placement of the ultrasound probe coupled to a guide system, the placement of the ultrasound probe positioning the guide system at the insertion point location;

verifying, from the image data, that the ultrasound probe coupled to the guide system is in a stable position at the insertion point location;

based on verification of the stable position of the ultrasound probe coupled to the guide system at the insertion point location, conditionally signaling a user for needle insertion; and tracking the interventional device from the insertion point location to the target structure.

2. The computer program product of claim 1, wherein segmenting the image data based upon appearance of the target structure processing the image data with temporally trained machine learning.

3. The computer program product of claim 1, wherein determining, from the segmented image data, the location of the target structure within the subject includes checking conflicting information based on a general configuration of anatomy of the subject at a location of the ultrasound probe acquiring the image data.

4. A computer program product comprising on one or more non-transitory computer storage media having stored thereon instructions that, when executed by one or more computing devices, cause the one or more computing devices to perform operations comprising:

accessing image data acquired from a subject using an ultrasound probe on a surface of the subject, the image data including a plurality of images of a target structure of the subject, the plurality of images including a plurality of views of the target structure;

determining, from the plurality of views, a location of the target structure within the subject;

identifying a critical structure from the plurality of views;

determining an insertion point location for an interventional device where the interventional device reaches the target structure from the insertion point location without penetrating the critical structure in the subject;

guiding placement of the ultrasound probe coupled to a guide system, the placement of the ultrasound probe positioning the guide system at the insertion point location;

verifying, from the image data, that the ultrasound probe coupled to the guide system is in a stable position at the insertion point location;

based on verification of the stable position of the ultrasound probe coupled to the guide system at the insertion point location, conditionally signaling a user for needle insertion; and tracking the interventional device from the insertion point location to the target structure.

5. The computer program product of claim 4, wherein the critical structure includes at least one of a bone, an unintended blood vessel, a non-target organ, or a nerve.

6. The computer program product of claim 4, wherein the plurality of images include images at a plurality of different timeframes.

7. The computer program product of claim 4, wherein determining, from the plurality of views, the location of the target structure within the subject includes checking conflicting information based on a general configuration of anatomy of the subject at a location of the ultrasound probe acquiring the image data.

8. A computer program product comprising one or more non-transitory computer storage media having stored thereon instructions that, when executed by one or more computing devices, cause the one or more computing devices to perform operations comprising:

accessing image data acquired from a subject using an ultrasound probe, the image data including at least one image of a target structure of the subject;

determining, from the image data, a location of the target structure within the subject;

determining an insertion point location for an interventional device based upon the location of the target structure;

guiding placement of the ultrasound probe coupled to a guide system, the placement of the ultrasound probe positioning the guide system at the insertion point location;

guiding the interventional device, via the guide system, into a field of view (FOV) of the ultrasound probe;

sending, to a display, guidance of the interventional device from the insertion point location to the target structure;

verifying, from the image data, that the ultrasound probe coupled to the guide system is in a stable position at the insertion point location; and based on verification of the stable position of the ultrasound probe coupled to the guide system at the insertion point location, conditionally signaling a user for needle insertion.

9. The computer program product of claim 8, wherein the instructions further include determining at least one of an angle for the interventional device from the insertion point location to the target structure, a rotational angle for the ultrasound probe with respect to the subject, or an insertion distance from the insertion point location to the target structure.

10. The computer program product of claim 8, wherein sending guidance to the display further includes sending, to the display, an indicator of at least one of an angle for the interventional device, the insertion point location, the location of the target structure, or an insertion distance.

11. The computer program product of claim 10, wherein the indicator includes the insertion point location projected proximate to the target structure, or a position of the ultrasound probe at the insertion point location.

12. The computer program product of claim 8, wherein the instructions further include tracking the interventional device from the insertion point location to the target structure, wherein sending guidance to the display includes providing real-time feedback to a user, via the display, based on tracking the interventional device.

13. The computer program product of claim 8, wherein the instructions for determining the location of the target structure within the subject include segmenting the image data based upon appearance of the target structure to determine at least one of the location of the target structure or identity of the target structure.

14. The computer program product of claim 8, wherein the target structure is one of an artery, a vein, a femoral artery, a femoral vein, a jugular vein, a peripheral vein, a subclavian vein, an airway, a lumen, a luminal organ, a body cavity, a fluid filled anatomic space, a location requiring biopsy, a breast, a kidney, a lymph node, a spinal canal, a location requiring nerve block, a peritoneal space or a pleural space.

15. The computer program product of claim 8, wherein accessing the image data includes receiving a plurality of images of the target structure of the subject acquired in real time.

16. The computer program product of claim 15, wherein the plurality of images include a plurality of views of the target structure, and the instructions further include assessing the plurality of views to identify a critical structure in the subject, and identifying a location on the subject where the interventional device reaches the target structure from the insertion point location without penetrating the critical structure in the subject.

17. The computer program product of claim 16, wherein the critical structure includes at least one of a bone, an unintended blood vessel, a non-target organ, or a nerve.

18. The computer program product of claim 16, wherein the plurality of images include images at a plurality of different timeframes.

19. The computer program product of claim 8, wherein determining, from the image data, the location of the target structure within the subject includes checking conflicting information based on a general configuration of anatomy of the subject at a location of the ultrasound probe acquiring the image data.

* * * * *